United States Patent [19]

Mikulicz et al.

[11] 4,225,737
[45] Sep. 30, 1980

[54] ALKYLATION PROCESS

[75] Inventors: Michael Z. Mikulicz, Palatine; James F. Himes, Mt. Prospect, both of Ill.

[73] Assignee: UOP Inc., Des Plaines, Ill.

[21] Appl. No.: 32,613

[22] Filed: Apr. 23, 1979

[51] Int. Cl.³ ............................................. C07C 2/66
[52] U.S. Cl. .................................... 585/449; 585/464
[58] Field of Search .............................. 585/449, 464

[56] References Cited

U.S. PATENT DOCUMENTS

| | | | |
|---|---|---|---|
| 3,483,265 | 12/1969 | Rakestraw et al. | 585/449 |
| 3,494,971 | 2/1970 | Fenske | 585/449 |
| 3,830,865 | 8/1974 | Anderson | 585/449 |
| 3,950,448 | 4/1976 | Witt | 585/449 |
| 4,046,516 | 9/1977 | Burton et al. | 585/449 |
| 4,072,730 | 2/1978 | Winter | 585/449 |

Primary Examiner—C. Davis
Attorney, Agent, or Firm—James R. Hoatson, Jr.; Robert W. Welch; William H. Page, II

[57] ABSTRACT

A process is disclosed for the alkylation of an aromatic hydrocarbon with an olefin-acting alkylating agent. The aromatic hydrocarbon is commingled with a first portion of said alkylating agent in a first alkylation reaction zone at alkylation reaction conditions in contact with a hydrofluoric acid catalyst. The acid phase of the effluent from the first alkylation reaction zone is separated, and the hydrocarbon phase, comprising alkylate and unreacted aromatic hydrocarbon is commingled with a second portion of said alkylating agent at alkylation reaction conditions in a second alkylation reaction zone in contact with a hydrofluoric acid catalyst separately charged thereto, the hydrofluoric acid catalyst being that separated from the effluent of the first alkylation reaction zone. The acid phase is separated from the effluent from the second alkylation reaction zone and recycled to the first alkylation reaction zone, and the alkylate product is recovered from the hydrocarbon phase.

7 Claims, 1 Drawing Figure

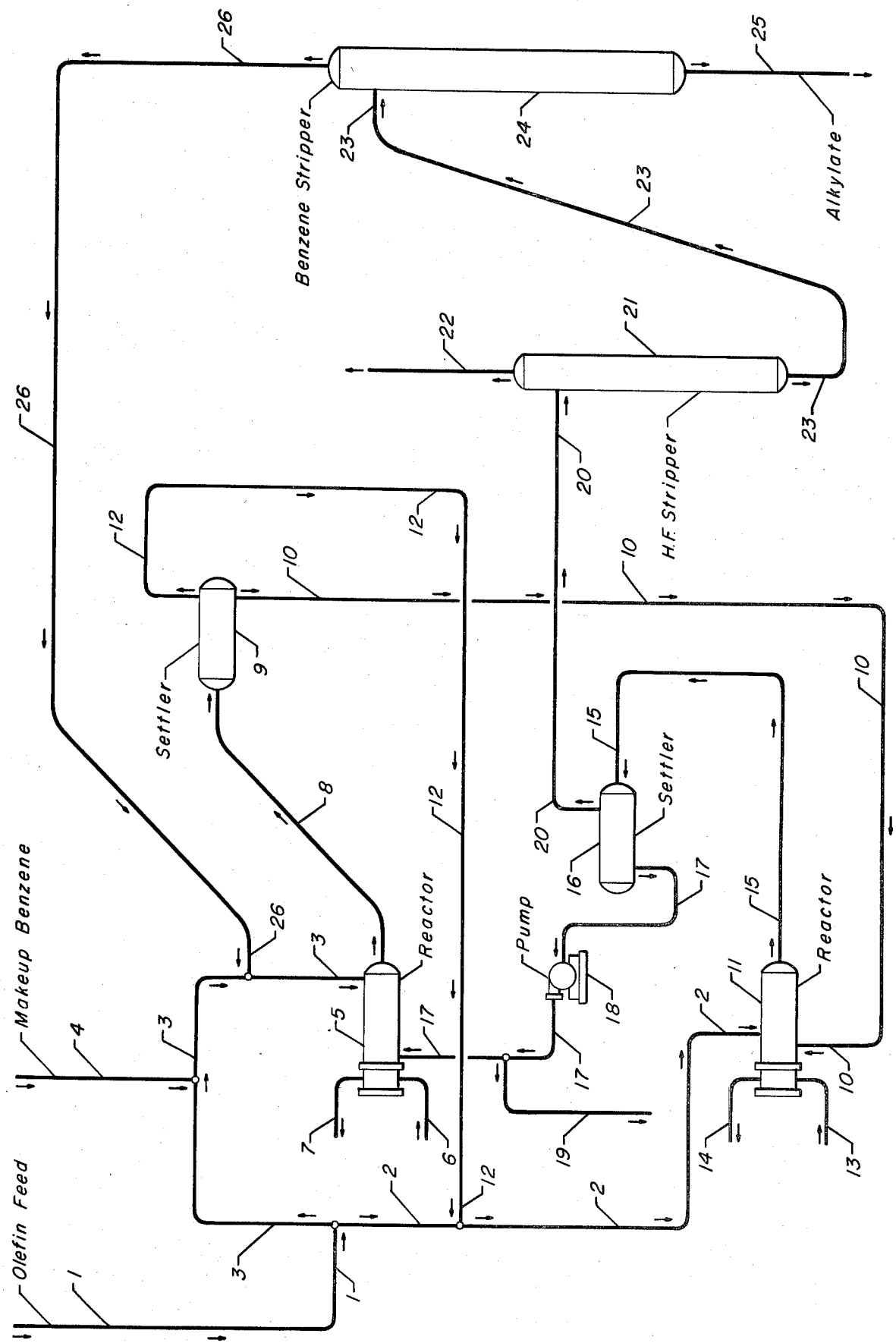

ALKYLATION PROCESS

This invention relates to a process for the alkylation of an aromatic hydrocarbon with an olefin-acting alkylating agent. More specifically, this invention relates to the hydrofluoric acid-catalyzed alkylation of an aromatic hydrocarbon with a $C_7$–$C_{15}$ olefin-acting alkylating agent to provide valuable alkylaromatic petrochemical products.

Processes for the acid-catalyzed alkylation of aromatic hydrocarbons with $C_7$–$C_{15}$ olefin-acting alkylating agents are of known importance to the petroleum and petrochemical industries. For example, said processes provide useful alkylaromatic intermediates in the manufacture of biodegradable detergents. One commercially significant process concerns the hydrofluoric acid-catalyzed alkylation of benzene, toluene, and the like, with a substantially straight chain $C_7$–$C_{15}$ monoolefin alkylating agent to provide a detergent grade alkylate especially useful in the manufacture of said biodegradable detergents.

In general, commercial processes for the alkylation of an aromatic hydrocarbon with an olefin-acting alkylating agent employ benzene, toluene, and the like, as the aromatic hydrocarbon, and the olefin-acting alkylating agent is frequently a $C_7$–$C_{15}$ monoolefin or mixtures thereof. Catalysts include hydrofluoric acid, sulfuric acid, and other acid or acid-acting catalysts such as anhydrous aluminum chloride. In a hydrofluoric acid-catalyzed alkylation process, the aromatic hydrocarbon, olefin-acting alkylating agent and hydrofluoric acid are admixed in an alkylation reactor and, after the reaction is substantially complete, the reaction mixture is recovered and allowed to settle into an acid phase and an acid immiscible hydrocarbon phase. The acid phase is separated and recycled to the alkylation reactor, and the hydrocarbon phase is further processed for the separation of unreacted aromatic hydrocarbon and the recovery of alkylate product. The separated aromatic hydrocarbon is recycled to the alkylation reactor to provide a major portion of the aromatic reactant therein.

In order to produce an acceptable yield of high quality alkylate in a commercial alkylation process, it has been found necessary to conduct the alkylation reaction at fairly specific alkylation reaction conditions such as temperature and pressure, and the concentration of both the catalyst and the reactants is of considerable importance. For example, although processing conditions relating to the hydrofluoric acid-catalyzed alkylation of aromatic hydrocarbons are generally more dependent on equilibrium considerations than are, for example, isoparaffin alkylation conditions, it has been found desirable to employ a large molar excess of aromatic hydrocarbon with respect to the olefin-acting alkylating agent in order to provide an adequate yield of high quality alkylaromatic product, and also as an aid to temperature control of the alkylation reaction mixture. While it is known that the quality of the alkylate is improved as the aromatic hydrocarbon/olefin-acting alkylating agent mole ratio is increased, the use of a large molar excess of aromatic hydrocarbon leads to economic and technical difficulties. For example, when benzene is alkylated with $C_7$–$C_{15}$ monoolefins, the large volume of unreacted benzene contained in the alkylation reactor effluent requires high capacity fractionation means entailing high capital and utilities cost. Failure to employ a large molar excess of the aromatic hydrocarbon leads to the formation of polyalkylaromatics, $C_7$–$C_{15}$ polymers, and other undesirable by-products difficult to separate from the desired alkylaromatic product. The process of the present invention is directed, in part, to a method for reducing the volume of aromatic hydrocarbon which must be separated from the alkylate and recycled, while at the same time maintaining the general quality and yield of the alkylaromatic product.

It is an object of the present invention to provide a process for the alkylation of an aromatic hydrocarbon with an olefin-acting alkylating agent.

It is a further object to provide a process for the hydrofluoric acid-catalyzed alkylation of an aromatic hydrocarbon with a substantially straight chain $C_7$–$C_{15}$ monoolefin to provide a detergent grade alkylate wherein a lesser amount of aromatic hydrocarbon is required to be separated from the alkylate and recycled to the alkylation reactor.

In one of its board aspects, the present invention embodies a process for the alkylation of an aromatic hydrocarbon with an olefin-acting alkylating agent which comprises commingling said aromatic hydrocarbon with a first portion of said olefin-acting alkylating agent at alkylation reaction conditions in a first alkylation reaction zone in contact with a hydrofluoric acid catalyst separately charged thereto; separating the acid phase of the effluent from said first alkylation reaction zone effluent and recovering a hydrocarbon phase comprising alkylate and unreacted aromatic hydrocarbon; commingling said hydrocarbon phase with a second portion of said olefin-acting alkylating agent at alkylation reaction conditions in a second alkylation reaction zone in contact with a hydrofluoric acid alkylation catalyst separately charged thereto, said hydrofluoric acid catalyst being that previously separated from the effluent of said first alkylation reaction zone; separating the acid phase of the effluent from said second alkylation reaction, and recycling said acid phase to said first alkylation reaction zone; and recovering the alkylation product from the hydrocarbon phase.

Other objects and embodiments of this invention will become apparent in the following detailed specification.

Closely related prior art is depicted in U.S. Pat. No. 3,830,865 which concerns an alkylation process, the practice of which affords a substantial reduction in the amount of the aromatic hydrocarbon reactant required to provide a molar excess with respect to a given amount of olefin-acting alkylating agent. By passing only a portion of the alkylating agent to a first alkylation reactor, a significantly smaller amount of aromatic hydrocarbon is required in the overall alkylation process. Thus, the hydrocarbon effluent from the first alkylation reactor, comprising unreacted aromatic hydrocarbon, is separated and charged to a second alkylation reactor, and said aromatic hydrocarbon is contacted therein with the remaining portion of the alkylating agent at alkylation reaction conditions. In this manner, although the amount of aromatic hydrocarbon required for the overall alkylation process is substantially reduced, there is provided a desired molar excess of said hydrocarbon to each of the alkylation reactors.

The attached drawing is a schematic illustration of an alkylation process representing one preferred embodiment of the present invention.

In this preferred embodiment, for purposes of illustration, the aromatic hydrocarbon is benzene and the olefin-acting alkylating agent is a mixture of substantially straight chain $C_7$–$C_{15}$ monoolefins hereinafter referred to as mixed olefins. It is not intended that the schematic drawing, nor the various reactants described with reference thereto, shall serve as an undue limitation on the generally broad scope of the invention as set out in the appended claims.

Referring then to the drawing, the mixed olefin feedstock is charged to the alkylation process by way of line 1. The mixed olefin feedstock is charged to the process at a rate to provide about 600 moles of mixed olefins per hour. The mixed olefin feedstock is equally divided into lines 2 and 3, each of said lines thus containing a flow of 300 moles of mixed olefins per hour. Make-up benzene is charged to the alkylation process via line 4 to be admixed with that portion of the mixed olefin feedstock diverted through line 3. The make-up benzene is charged at a rate of about 334 moles per hour.

The hydrocarbon reactant mixture is continued through line 3 together with recycled benzene from line 26 and charged to a first alkylation reactor 5. The recycled benzene from line 26 is supplied at a rate of about 2,366 moles per hour. The total hydrocarbon charged to the alkylation reactor 5 will thus include about 300 moles of mixed olefins and 2,700 moles of benzene per hour. The benzene will therefore be charged to the alkylation reactor 5 in about a 9:1 mole ratio with the mixed olefins charged thereto. The combined feed is charged to the alkylation reactor 5 and admixed with the hydrofluoric acid alkylation catalyst to form an alkylation reaction mixture therein having an acid/hydrocarbon volume ratio of from about 1 to about 2. The hydrofluoric acid alkylation catalyst is charged to the alkylation reactor 5 from line 17 and comprises about 85 wt.% acid and less than about 1 wt.% water. The remainder comprises organic matter common to said alkylation catalyst. The alkylation reaction conditions in the first alkylation reactor 5 include a temperature of from about 90° to about a 100° F. and a pressure sufficient to maintain substantially liquid phase reaction conditions. Cooling water is charged through line 6 and travels through the alkylation reactor 5 in indirect heat exchange relationship with the alkylation reaction mixture contained therein. The cooling water is discharged through line 7. After a contact time of from about 0.1 to about 5 minutes, the alkylation reaction mixture is withdrawn from the first alkylation reactor 5 and transferred through line 8 to a settler 9. The reaction mixture is allowed to stand in the settler 9 and separate into an upper hydrocarbon phase and a lower hydrofluoric acid phase. The hydrofluoric acid is withdrawn from the bottom of settler 9 and routed to a second alkylation reactor 11 by way of line 10.

Referring back to settler 9, the upper hydrocarbon phase recovered therein, representing the total hydrocarbon effluent from the first alkylation reactor 5, is withdrawn overhead through line 12 and is continued through line 12 to provide about 2,400 moles of benzene and 300 moles of alkylate per hour to be commingled with that portion of the mixed olefin feedstock previously diverted through line 2 from line 1. The combined hydrocarbon streams will thus afford a flow of 2,400 moles of benzene, 300 moles of mixed olefins and 300 moles of alkylate per hour, and this combined hydrocarbon stream is continued through line 2 and constitutes the total hydrocarbon charge to the second alkylation reactor 11. The benzene/olefin mole ratio in said second alkylation reactor 11 will thus be about 8. The alkylation reaction conditions employed in the second alkylation reactor 11 are substantially as described with respect to the first alkylation reactor 5, except that a pressure differential of about 15 psig. is maintained to facilitate the transfer of the hydrofluoric acid catalyst to the second alkylation reactor 11, as well as the transfer of the hydrocarbon effluent from the settler 9. The heretofore mentioned hydrofluoric acid from line 10 is charged to the second alkylation reactor 11 and intimately admixed with the hydrocarbon feed from line 2 to form an alkylation reaction mixture therein. Cooling water, charged through line 13, is passed in indirect heat exchange relationship with the alkylation reaction mixture contained in the alkylation reactor 11, and the water is then discharged through line 14. The alkylation reaction mixture is withdrawn from the alkylation reactor 11 after a contact time of from about 0.1 to about 5 minutes and passed to a settler 16 by way of line 15. The reaction mixture is retained in the settler 16 free of agitation to facilitate separation of the immiscible hydrocarbon and acid phases therein. The hydrofluoric acid catalyst which settles out as the lower liquid phase is recovered from the bottom of the settler 16 through line 17 and recycled by means of pump 18 to the first alkylation reactor 5 for further use therein. It is contemplated that the hydrofluoric acid catalyst will require regeneration, continuously or intermittently, with continued use. This can be effected by taking a slip stream from line 17 and withdrawing the slip stream through line 19 for transfer to conventional regeneration means. the regeneration means, being conventional regeneration means and not essential to an understanding of the present invention, are not shown.

In any case, the hydrocarbon phase recovered in settler 16 is withdrawn overhead through line 20 and transferred to a hydrofluoric acid stripper 21. About 2,100 moles of benzene, and 600 moles of alkylate are transferred to the hydrofluoric acid stripper 21 through line 20 per hour. In the hydrofluoric acid stripper, hydrofluoric acid is recovered overhead through line 22. This relatively highly concentrated hydrofluoric acid may be recovered or recycled to line 10 to line 17 for use in the alkylation reactors 5 and/or 11. In any case, a hydrocarbon phase is withdrawn from the hydrofluoric acid stripper 21 and transferred to a benzene stripper 24 by way of line 23. The vessel employed as a benzene stripper is a fractionation column containing the conventional trays, reboiling means, refluxing means, and the like, all of which are well-known to the art. The product alkylate is recovered from the benzene stripper 24 as a bottoms fraction through line 25 at a rate of about 600 moles per hour. The benzene fraction is taken overhead and recycled to the first alkylation reactor 5 by way of line 26 at a rate of about 2,366 moles per hour. It is understood that the benzene feedstock and the mixed olefin feedstock will typically contain various amounts of hydrocarbon impurities, e.g., $C_7$–$C_{15}$ paraffinic hydrocarbons, cyclohexane, and the like, requiring further fractionation of the hydrofluoric acid stripper hydrocarbon effluent. The necessary fractionation means, being conventional and well-known to the art, are not essential to an understanding of the present invention, and are not shown.

The foregoing description illustrates some of the advantages of the present invention when embodied in a hydrofluoric acid-catalyzed benzene-olefin alkylation process. In keeping with the prior art dual-reactor system, reaction conditions of the first alkylation reactor 5 and the second alkylation reactor 11 include a desirably high benzene/olefin mole ratio of about 9:1 which is conducive to improved alkylate product quality. Yet fractionation requirements in the benzene stripper 24 need only be sufficient to separate benzene equivalent to an overall benzene/olefin mole ratio of less than about 5:1. Thus, the alkylate product quality is equal or superior to alkylate produced by the more conventional alkylation processes, while the fractionation requirements are substantially reduced with attendant savings in capital and utilities cost. By contrast, alkylate produced in conventional hydrofluoric acid-catalyzed alkylation processes using an overall benzene/olefin mole ratio of about 5:1 would be of relatively low quality and recovered in lower yield. The alkylation process of the present invention embodies the improvements and advantages of the prior art process, and offers a further savings in capital and utilities cost, which savings are attributable to improved hydrofluoric acid circulation and a substantial reduction in the hydrofluoric acid inventory of the process. Other advantages are to be derived from the practice of this invention. For example, in the course of the alkylation process, the hydrofluoric acid catalyst tends to accumulate and become diluted with certain organic materials which are largely polymeric by-products of the alkylation reaction. This necessitates at least periodic regeneration of the acid catalyst to maintain a desired acid concentration. It has been observed that the second alkylation reactor of a dual reactor system produces a lesser amount of said organic material than does the first reactor. In any case, those prior art processes employing a dual reactor system, each of which embodies an independent acid catalyst recycle system in an otherwise interacting alkylation system, experience undue difficulty in maintaining a desired acid concentration in each of said independent recycle systems. By processing the hydrofluoric acid in accordance with the present invention, this difficulty is substantially obviated.

The preferred aromatic hydrocarbons for use in the present invention are the alkylatable monocyclic aromatic hydrocarbons including benzene, toluene, the xylenes, cumene, ethylbenzene, and the like. Alkylatable polycyclic aromatic hydrocarbons such as naphthalene, anthracene, phenanthrene, etc., are also suitably alkylated utilizing the process of this invention. Of the alkylatable aromatic hydrocarbons, benzene is preferred.

The olefin-acting alkylating agents herein contemplated are characterized as $C_7$-$C_{15}$ olefin-acting alkylating agents. These include the $C_7$-$C_{15}$ alkyl halides, but especially the $C_7$-$C_{15}$ substantially straight chain monoolefins, for example heptene, octene, nonene, decene, undecene, dodecene, tridecene, tetradecene, pentadecene, and mixtures thereof. The selected olefin-acting alkylating agent may be utilized admixed with non-reactive hydrocarbons, for example $C_7$-$C_{15}$ paraffins, in any proportion.

The alkylation catalyst employed herein is preferably a hydrofluoric acid alkylation catalyst generally containing about 75 wt.% or more of titratable acid, about 5 wt.% or less of water, with organic diluents constituting the remainder. A particularly preferred catalyst comprises about 85 wt.% hydrofluoric acid and less than about 1 wt.% water.

In general, alkylation reaction conditions suitable for use in the present process, in which the aromatic hydrocarbon is preferably benzene, include a temperature of from about 0° to about 200° F., a contact time between the catalyst and reactants of from about 0.1 to about 30 minutes, and a pressure sufficient to maintain substantially liquid phase reaction conditions. A pressure differential of from about 5 to about 20 psig. is preferably maintained between the alkylation reaction zones to facilitate the transfer of hydrofluoric acid catalyst, and also hydrocarbon effluent streams, as herein contemplated. In one preferred embodiment, a catalyst/hydrocarbon volume ratio of from about 0.1 to about 10 is employed, and the temperature is maintained at from about 90° to about 100° F.

The reaction mixture recovered from the alkylation reactors may be passed through a reaction mixture soaker as is commonly practiced, and it is intended that both the alkylation reactor and the reaction mixture soaker be included within the scope of the term "alkylation reaction zone." Suitable reaction mixture soakers are well known in the art. For example, the reaction mixture soakers described in U.S. Pat. No. 3,560,587 and U.S. Pat. No. 3,607,970 may suitably be employed in the present process. Such reaction mixture soakers are typically vessels equipped with perforated trays, baffle sections, and the like, to maintain the reaction mixture of catalyst and hydrocarbon charged from the alkylation reactor as a fairly homogeneous mixture or emulsion for a predetermined length of time. The mixture of catalyst and hydrocarbons is maintained in the reaction mixture soaker for a time which depends on the composition of the reaction mixture. A reaction mixture soaker residence time of from about 1 to about 30 minutes is preferred. The temperature and pressure maintained in the reaction mixture soaker are the same as the temperature and pressure maintained in the alkylation reactor.

Separation of the alkylation reaction mixture into a hydrocarbon phase and an acid catalyst phase is typically effected by allowing the alkylation reaction mixture effluent from the alkylation reactor or soaker to stand under quiescent conditions whereby the acid catalyst settles out from the hydrocarbon phase comprising unreacted aromatic hydrocarbon and alkylate product. The hydrocarbon phase is then easily mechanically separated from the acid catalyst phase. The temperature and pressure employed in such a settling operation are substantially the same as those described above in connection with the alkylation reaction conditions. The hydrocarbons and the catalyst are preferably maintained in the liquid phase during the separation operation.

Some means for withdrawing heat from the alkylation reactor is necessary for operation of the process. A variety of means for accomplishing heat withdrawal are well known. For example, the heat generated in the alkylation reaction may be withdrawn directly from the alkylation reactor by indirect heat exchange between cooling water and the reaction mixture in the reactor.

The hydrocarbon effluent stream recovered from the first alkylation zone, by settling the reaction mixture to separate the catalyst, is combined with a second portion of the olefin-acting alkylating agent and charged to the second alkylation reactor, wherein the combined olefin and hydrocarbon effluent are contacted with the alkylation catalyst. It is contemplated that sufficient aromatic hydrocarbon is charged to the first alkylation zone so that no further aromatic hydrocarbon make-up, or aromatic hydrocarbon recovered from fractionation, need be added to the hydrocarbons charged to the second reactor. Under some conditions, it may be advantageous to charge some further fresh aromatic hydrocarbon to the second alkylation reactor, and such a modification is within the scope of the present process.

In general, the benefits and advantages of the present process are provided when the aromatic hydrocarbon reactant is charged into a series of at least two separate alkylation reaction zones and contacted with at least two different portions of the olefin-acting alkylating agents. One obvious modification of the present process is to divide the olefin-acting alkylating agent into a plurality of portions, e.g., three or more. The aromatic hydrocarbon and a first portion of the olefin-acting alkylating agent are contacted in a first alkylation zone and the hydrocarbons are separated from the first catalyst to form the hydrocarbon effluent stream. The hydrocarbon effluent from the first alkylation zone is then contacted with a second portion of the olefin-acting alkylating agent in the second alkylation zone. The hydrocarbon effluent recovered from the second alkylation zone is contacted with a third portion of the olefin-acting alkylating agent in a third alkylation zone, etc. The hydrocarbon effluent from the last alkylation zone in the series provides a reaction product stream which is fractionated to recover the alkylation reaction product and to separate the isoparaffin contained therein for recycle to the first alkylation reaction zone.

In a preferred embodiment wherein the olefin-acting alkylating agent is divided into two portions, it is preferred that neither portion contain less than about 10 vol.% of the whole. For example, in a continuous operation, the first portion may be fed to the first alkylation reaction zone at a rate of about 10 moles per hour. The second portion being then fed to the second alkylation reaction zone at a rate of at least about 1 mole per hour and not in excess of about 100 moles per hour. Preferably, the two portions do not vary by more than from about 1-5 to about 5-1. Best results are achieved when the two portions contain roughly equimolar amounts of the olefin-acting alkylating agent. In this manner, the amount of aromatic hydrocarbon required to provide an optimum molar excess in each alkylation reaction zone is maintained at a minimum, and the highest quality product can be produced in each of the alkylation reaction zones.

We claim as our invention:

1. A process for the alkylation of an aromatic hydrocarbon with an olefin-acting alkylating agent which comprises:
    (a) commingling an aromatic hydrocarbon and a first portion of said olefin-acting alkylating agent at alkylation reaction conditions in a first alkylation reaction zone in contact with a hydrofluoric acid catalyst;
    (b) separating the effluent from said first alkylation reaction zone into an acid phase and a hydrocarbon phase comprising alkylate and unreacted aromatic hydrocarbon;
    (c) commingling said hydrocarbon phase with a second portion of said olefin-acting alkylating agent at alkylation reaction conditions in a second alkylation reaction zone in contact with said acid phase transferred from said first to said second reaction zone by maintaining a pressure differential between the first and second zones of from about 5 to about 20 psig.;
    (d) separating the effluent from said second alkylation reaction zone into an acid phase and a hydrocarbon phase and recycling the former to said first alkylation reaction zone; and,
    (e) recovering an aromatic alkylation product from the last-mentioned hydrocarbon phase.

2. The process of claim 1 further characterized in that said aromatic hydrocarbon is a monocyclic aromatic hydrocarbon.

3. The process of claim 1 further characterized in that said aromatic hydrocarbon is benzene.

4. The process of claim 1 further characterized in that said olefin-acting alkylating agent is a $C_7$–$C_{15}$ monoolefin.

5. The process of claim 1 further characterized in that said olefin-acting alkylating agent is a substantially straight chain $C_7$–$C_{15}$ monoolefin.

6. The process of claim 1 further characterized in that from about 20 to about 80 volume percent of the olefin-acting alkylating agent is commingled with said aromatic hydrocarbon in said first alkylation reaction zone.

7. The process of claim 1 further characterized in that the alkylation reaction conditions in said first alkylation reaction zone and said second alkylation reaction zone include a pressure sufficient to maintain a substantially liquid phase reaction mixture.

* * * * *